United States Patent [19]

Fraser

[11] Patent Number: 5,078,494
[45] Date of Patent: Jan. 7, 1992

[54] GLOW DISCHARGE CHAMBER AND GAS FLOW SYSTEM FOR GLOW DISCHARGE EMISSION SPECTROMETER

[76] Inventor: Robert B. Fraser, 11113 NE. 38th Pl., Bellevue, Wash. 98004

[21] Appl. No.: 685,170

[22] Filed: Apr. 15, 1991

Related U.S. Application Data

[63] Continuation-in-part of Ser. No. 575,893, Aug. 31, 1990, abandoned.

[51] Int. Cl.$^5$ ............................................. G01N 21/69
[52] U.S. Cl. ................................... 356/311; 356/313; 356/417
[58] Field of Search ................ 356/311, 313, 314, 316, 356/417

[56] References Cited

U.S. PATENT DOCUMENTS

| | | | |
|---|---|---|---|
| 3,951,607 | 4/1976 | Fraser | 250/226 |
| 3,996,010 | 12/1976 | Fraser | 250/226 |
| 4,845,041 | 7/1989 | Scuitto et al. | 356/11 |

OTHER PUBLICATIONS

"Glow Discharge Optical Spectroscopy for Monitoring Sputter Deposited Film Thickness", J. Vac Sci Techno., vol. 10, No. 6, pp. 1144–1149, Green et al.
"Glow Discharge Optical Spectroscopy Measurement of Dopant Concentration in a-Si:H*", J. of Non-Crystalline Solids, 35 & 36, pp. 273–277, Zetch et al.
"New Method of Respiratory Gas Analysis: Light Spectrometer", American Physiological Society, 1985, Robert B. Fraser and Stephen Z. Turney.
"A New Method for Respiratory Monitoring During Space Flight", NASA Final Technical Report No. NWRA-CR-89-R048, Aug. 31, 1989, of later, Robert B. Fraser.
Greene et al., J. Vac. Sci. Technol., vol. 10, No. 6, Nov./Dec. 1973, pp. 1144–1149.
Zesch et al., Journal of Non-Crystalline Solids, 35 & 36 Jan.-Feb. 1980, pp. 273–277.

Primary Examiner—F. L. Evans

[57] ABSTRACT

A glow discharge chamber for a glow discharge emission spectrometer has a housing with a cavity. The cavity has a gas inlet and a gas outlet. The gas outlet is adapted to be connected to a vacuum pump to produce flow of gas through the cavity. An anode is located within the cavity adjacent to the gas outlet. A cathode is located in the cavity and gas within the cavity emits negative glow radiation adjacent to the cathode when a voltage differential between the anode and cathode exists. A radiation transmissive, gas retaining window in the housing through which negative glow radiation passes from the cavity to one or more radiation sensors for spectral analysis. The flow of gas through the cavity channels sputtered cathode oxides away from the window due to the cathode and anode arrangement in the cavity.

19 Claims, 4 Drawing Sheets

FIG. 5

GLOW DISCHARGE CHAMBER AND GAS FLOW SYSTEM FOR GLOW DISCHARGE EMISSION SPECTROMETER

This application is a continuation-in-part of application Ser. No. 07/575,893 filed Aug. 31, 1990 now abandoned, the benefit of the filing dates of which are hereby claimed under 35 USC 120.

BACKGROUND OF THE INVENTION

This invention relates to multi-gas analysis in general, and specifically to multi-gas analysis of respiration by glow discharge emission spectrometry.

Respiratory monitoring allows analysis of physiological parameters including pulmonary blood flow, cardiac output, oxygen consumption, and anaerobic threshold. These physiological parameters are relevant for monitoring individuals in the fields of health care and athletic training, and especially during space flight where weightlessness dramatically affects these parameters.

Respiratory monitoring measures the above physiological parameters by analyzing the oxygen, nitrogen and carbon dioxide levels, among others, in the individual's respiration. The multi-gas analyzer commonly used for respiratory monitoring is the mass spectrometer which, however, is subject to random filament failure and requires a two-stage high vacuum system which can be troublesome during start-up. The measurement of all three of these gasses with the combination of three separate analyzers would lead to a number of difficulties, including a very bulky assembly, the reliability and maintenance of three separate analyzers, and the problem of matching three different response curves and lag times.

U.S. Pat. No. 3,951,607 and U.S. Pat. No. 3,996,010, both issued to Robert B. Fraser, disclose glow discharge emission spectrometers that function with a simple glow discharge transducer requiring only a moderate vacuum. The operation of the glow discharge emission spectrometer is based on the fact that when a gas sample is introduced into a low-pressure chamber in an electric field under the proper conditions of pressure, voltage, and chamber geometry, a glow discharge is formed. Selected spectral bands exist near the cathode region of this discharge (the negative glow) where the intensity of emission is proportional to the concentration of the component of interest in that gas sample. Monitoring the intensities of these bands provides a continuous measure of the component gas concentrations.

The glow discharge emission spectrometer of these two patents solve many of the above mentioned problems, however they require a large gas flow system (due to a high-flow vacuum control system) and a large, complex calibration system. Therefore, these spectrometers are too large and bulky for use in limited space environments, such as, for example, space craft.

Furthermore, the spectrometers of the above patents suffer from reduction of the transparency of the windows of the glow discharge chamber through which the negative glow radiation passes for spectral analysis. The sampled gas always contains oxygen. The high energy of the discharge causes the flow of oxygen ions to strike the cathode and produce an oxide of the cathode metal. This cathode oxide is sputtered off and deposited on the walls of the glow discharge chamber as well as on the windows.

The present invention provides a glow discharge chamber having a geometric configuration and anode and cathode orientation which minimizes the above cathode oxide sputtering. Furthermore, this glow discharge chamber allows calibration of the glow discharge emission spectrometer using fewer steps and few gasses than previously required, thus resulting in a less complex, smaller spectrometer. Specifically, calibration known in the art requires spectral analysis of seven different combinations of three gasses ($O_2$, $N_2$, and $CO_2$) while the calibration method of the present invention employs only two different gas combinations employing $O_2$, $N_2$ and $CO_2$.

Furthermore, the gas flow system of the present invention is a low-flow vacuum control system that reduces the overall size of the spectrometer.

SUMMARY OF THE INVENTION

The present invention is a glow discharge chamber and an associated gas flow system for a glow discharge emission spectrometer. The glow discharge chamber of the present invention has a specific chamber geometry and anode/cathode orientation that minimizes the deposition of sputtered cathode oxides onto the glow discharge chamber window.

The glow discharge chamber includes a housing with a cavity. The cavity has a gas inlet and gas outlet. The gas outlet is adapted to be connected to a vacuum pump to produce flow of ga through the cavity.

Adjacent to the gas outlet, there is an anode within the cavity. A cathode is located in the cavity and the gas within the cavity emits negative glow radiation at a location near the cathode when a voltage differential is created between the anode and cathode.

A radiation transmissive, gas retaining window in the housing allows negative glow radiation to pass from the cavity to one or more radiation sensors for spectral analysis.

The gas flow from the gas inlet, through the cavity, and out of the gas outlet channels sputtered cathode oxides away from the window due to the geometric configuration of the cavity and the cathode-anode arrangement within the cavity.

In a preferred embodiment, a plurality of gas inlets are located adjacent to a plurality of windows such that gas flow from the gas inlets shields the windows from cathode oxide sputtering and channels the sputtered oxides away from the windows and out of the gas outlet.

In another preferred embodiment, the cathode is made of titanium, molybdenum or their carbides to minimize the amount of sputtered cathode oxides produced and the housing is made of non-conductive material.

The geometric configuration of the cavity of this embodiment minimizes the amount of steps and gasses required to calibrate a glow discharge spectrometer. A background gas, preferably comprised of about 20 percent oxygen and 80 percent nitrogen, is first passed through the glow discharge chamber for spectral analysis. Next, a span gas, preferably comprised of about 95 percent oxygen and about 5 percent carbon dioxide is passed through the glow discharge chamber for spectral analysis.

The gas flow system associated with the above glow discharge chamber of the present invention allows construction of compact (about 1.5 cu. ft.) and simple glow discharge emission spectrometer operating at a pressure (preferably of about 0.600 torr) and total gas flow rate $Q_T$ (preferably about 125 cubic centimeters per second to about 500 cubic centimeters per second) suitable for a sustained glow discharge. This gas flow system includes a pump for providing relatively low pressure and a gas line connecting this pump to the gas outlet of the glow discharge chamber. A control valve in the gas line allows adjustment of the cross-sectional area of the gas line to alter either the glow discharge chamber pressure to maintain a substantially constant gas flow rate, or to alter the gas flow rate to maintain a substantially constant chamber pressure.

In the preferred embodiment of the gas flow system, the control valve is an electrically controlled solenoid. A pressure transducer responsive to pressure changes in the glow discharge chamber sends electrical signals to control circuitry. The control circuitry actuates the solenoid valve to vary the cross-sectional area of the gas line in order to maintain substantially constant pressure in the glow discharge chamber.

BRIEF DESCRIPTION OF THE DRAWINGS

A more complete appreciation of the invention may be had by reference to the accompanying drawings illustrating preferred embodiments of the invention to be described in detail, wherein.

DETAILED DESCRIPTION OF THE PREFERRED EMBODIMENT

Figure 1:
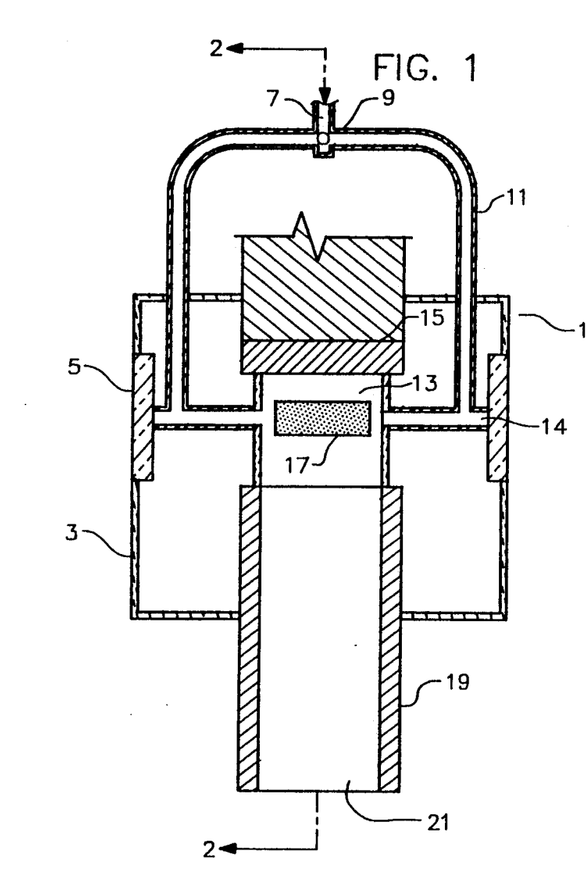
FIG. 1 is a cross-sectional view of the preferred embodiment of the glow discharge chamber of the present invention.
Figure 2:
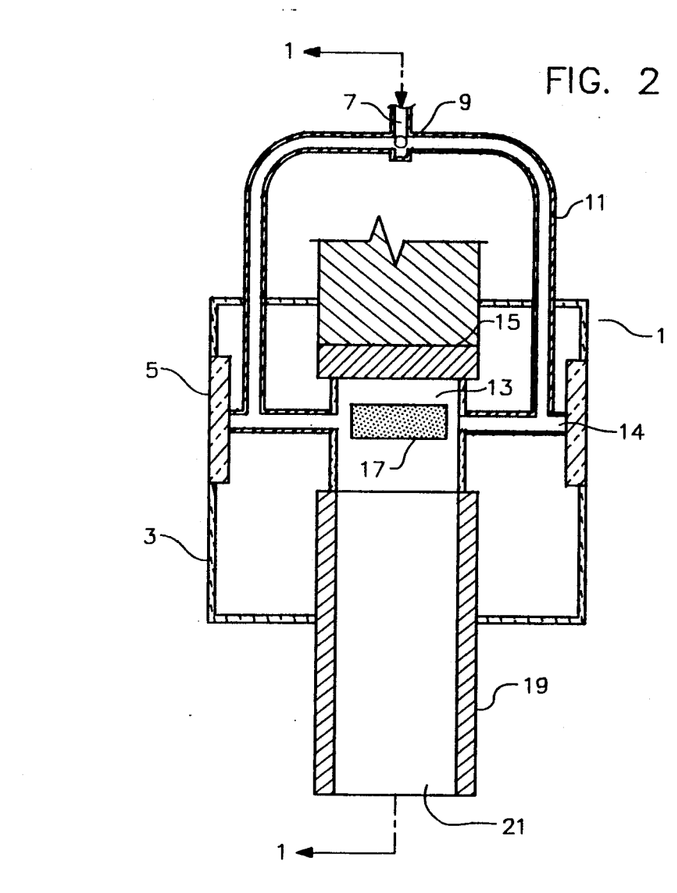
FIG. 2 is another cross-sectional view of the preferred embodiment of the glow discharge chamber of the present invention taken 90 degrees from FIG. 1.

FIG. 1 and FIG. 2 show the preferred embodiment of the glow discharge chamber 1 of the present invention. Glow discharge chamber 1 includes a housing 3, preferably comprised of non-conductive material to impede sputtered cathode oxides. Fitted in housing 3 are radiation transmissive, gas retaining windows 5. The windows 5 are four in number in the preferred embodiment, (one each for oxygen, nitrogen, carbon dioxide and water vapor spectral analysis), however a fewer or greater number of windows may be employed depending on the number of elemental gas components to be analyzed in the gas mixture. Windows 5 are preferably made of radiation transmissive material such as, for example, quartz or Pyrex.

Main gas inlet 7 receives the gas sample from a breathing tube (not shown) into which an individual exhales. Main gas inlet 7 is connected to manifold 9, which is preferably comprised of four secondary gas inlets 11. However, a fewer or greater number of secondary gas inlets 11 may comprise manifold 9 depending upon the number of elemental gas components to be analyzed in the gas mixture.

Secondary gas inlets 11 each join cavity 13 (chamber B) of housing 3 in one of passages 14 (chambers A). Four passages 14 (chambers A) are preferably employed, but more or less can also function with the present invention. Secondary gas inlets 11 each join one of passages 14 adjacent to one of windows 5. As shown in FIG. 1 and 2 and discussed in further detail below, this orientation of secondary gas inlet 11 proximate to windows 5 causes non-axial gas flow Q to both shield windows 5 from sputtered cathode oxides and to channel these sputtered cathode oxides away from windows 5 and out of the cavity 13.

Within cavity 13 (chamber B) is cathode 15, oriented such that negative glow radiation 17 of the sample gas located adjacent to cathode 15 passes through passages 14 (chambers A) of cavity 13 (chamber B) and through windows 5 for spectral analysis. It is readily apparent that each combination of window 5 and passage 14 (chamber A) is preferably physically separate from all other windows 5 and passages 14 (chambers A) for separate spectral analysis through each window 5.

Cathode 15 is preferably comprised of titanium, but may also be made of molybdenum or carbides of either of the above two. Titanium is preferred because it produces the least sputtered material and remains free of oxide for the greatest period of time. Specifically, following discharge with room air as the sampled gas at 0.6 torr, titanium did not show corrosion until 1000 to 2000 hours of operation, because titanium can absorb as much as 30 percent atomic oxygen near the cathode surface. Molybdenum is also desirable because it resists corrosion by anesthetic gasses known in the art such as halothane and ethrane.

Also within cavity 13 (chamber B) is anode 19 which, in the preferred embodiment, is adjacent to gas outlet 21. A voltage differential between cathode 15 and anode 19 causes the previously discussed negative glow radiation 17 adjacent to cathode 15. Gas outlet 21 is connected to the gas flow system of the present invention described below and shown in FIG. 4. Specifically a vacuum pump down stream from gas outlet 21 draws non-axial gas flow Q, (of each of passages 14 (chambers A)) and cathode oxides, away from windows 5, past cathode 15 and through gas outlet 21 adjacent anode 19. Thus, the orientation of cathode 15 and anode 19 within cavity 13 prevents obstruction of windows 5, due to cathode oxide sputtering at cathode 15, by channeling the non-axial gas flow Q of each of passages 14 (chambers A) away from windows 5.

In operation, an individual exhales into the breathing tube connected to main gas inlet 7. The gas sample passes through secondary gas inlets 11 of manifold 9 and enters passage 14 of cavity 13 adjacent to windows 5 such that the non-axial gas flow Q of each of passages 14 (chambers A) shields windows 5 from sputtered cathode oxides emanating from cathode 15 and channels the sputtered cathode oxide towards the lower pressure area at anode 19 and gas outlet 21 caused by the vacuum pump of the gas flow system described below. The negative glow radiation 17 of the sample gas caused by a voltage differential between cathode 15 and anode 19 passes through passages 14 (chambers A) and through windows 5. Spectral analysis of the negative glow radiation 17 of the gas sample is performed by detector/filter components described below and shown in FIG. 3.

Figure 3:
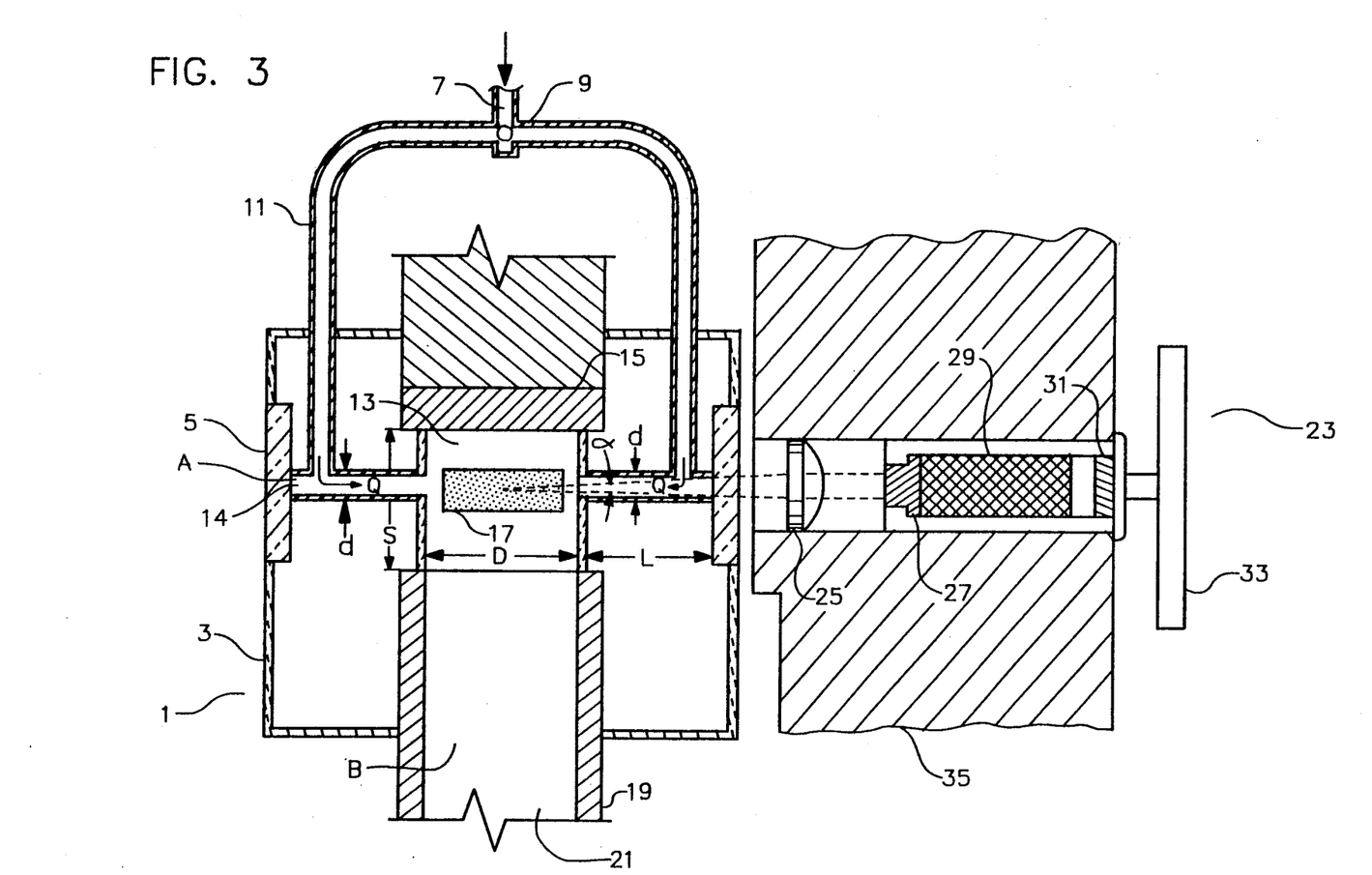
FIG. 3 is a cross-sectional view of the preferred embodiment of the glow discharge chamber of the present invention in combination with an exemplary glow discharge emission spectrometer detector/filter component.

Specifically, FIG. 3 shows the preferred embodiment of the glow discharge chamber 1 of the present invention aligned with one detector/filter component 23. Only one detector/filter component 23 is shown for the sake of brevity, but it is readily apparent that numerous detector/filter components 23, preferably one aligned with each window 5, can be employed. In this preferred embodiment, four detector/filter components are employed, one each for oxygen, nitrogen carbon dioxide and water vapor spectral analysis.

Glow discharge chamber 1 is oriented with detector/filter component 23 such that negative glow radiation 17 passes through passage 14 (chamber A) and through window 5 of glow discharge chamber 1 and through plano-convex lens 25, through quartz window 27, through optical interference filter 29, and into silicon detector 31 of the detector filter component 23. The output of silicon detector 31 is converted into a high-level signal (0-5 V) by a current-to-voltage converter (high-gain amplifier) 33 having extremely low noise characteristics. Temperature controlled housing 35 maintains detector/filter component 23 at a substantially constant temperature to minimize detector sensitivity and accuracy fluctuations.

Figure 4:
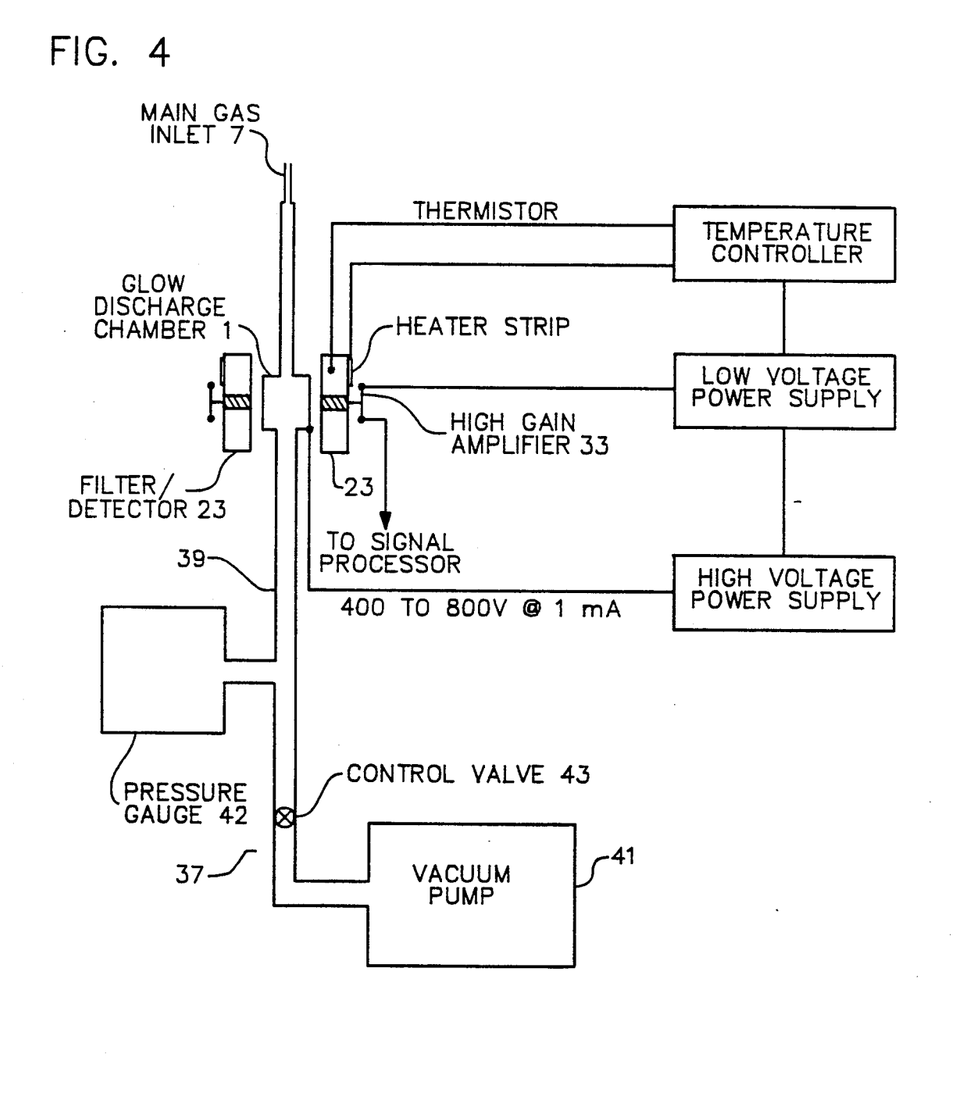
FIG. 4 is a schematic view of the glow discharge chamber and associated gas flow system.

As shown in FIG. 4, the glow discharge chamber 1 of the present invention is combined with gas flow system 37 for low-flow vacuum control of the gas sample within glow discharge chamber 1 at a glow discharge chamber pressure of preferably about 0.600 torr and a total sample gas flow rate $Q_T$ of preferably about 125 cubic centimeters per second to about 500 cubic centimeters per second. Total sample gas flow rate $Q_T$ is composed of all of the gas flow rates Q of passages 14 (chambers A), and preferably four chambers A are used. However, it will be understood that the present invention functions with a total gas flow rate $Q_T$ from about 0.1 cubic centimeters per second to about 1000 cubic centimeters per second and a glow discharge chamber pressure of about torr 0.1 to about 10.0 torr.

Gas flow system 37 includes gas line 39 that connects gas outlet 21 of glow discharge chamber 1 to vacuum pump 41. Vacuum pump 41 is preferably a dual-stage rotary-seal vacuum pump, for example the ULVAC G-10D, having the capability of preferably maintaining the glow discharge chamber pressure at about 0.600 torr±0.005 torr with a sample total gas flow rate $Q_T$ of about 125 cubic centimeters per second to about 500 cubic centimers per second.

Control valve 43 is in gas line 39 between outlet 21 and vacuum pump 41. Because flow samples at the main gas inlet 7 can vary due to contamination by dust or condensation, control value 43 controls the flow at vacuum pump 41 in order to maintain the glow discharge pressure at substantially 0.6 torr±0.005 torr. Control valve 43, for example the Whitey Valve No. B-18 RF8, allows adjustment of glow discharge pressure from about 0.4 to about 0.7 torr±0.005 torr at a substantially constant sample gas flow rate at an atmospheric inlet of about 6 milliliters/minute at about 298° K and 760 torr, and also allows adjustment of sample gas flow rate at an atmospheric inlet from about 3 milliliters/minute to about 7 milliliters/minute at about 298° K and 760 torr while maintaining a substantially constant glow discharge chamber pressure of about 0.6 torr±0.005 torr.

In an alternate embodiment, valve 41 is an electrically controlled solonoid valve, for example Brooks Instruments Model No. 5835, that operates off of a feed back system. A pressure transducer (gauge) 42 responsive to pressure changes in glow discharge chamber 1 sends electrical signals to control circuitry (not shown). The control circuitry activates the valve 43 to vary the cross-sectional area of gas line 39 in order to maintain substantially constant pressure (any pressure between about 0.1 torr and about 10.0 torr±0.005 torr) in glow discharge chamber 1.

Now referring to FIGS. 1-6, preferred dimensions of the glow discharge chamber 1 of the present invention are described. Specifically, glow discharge chamber 1 includes at least one first chamber A (passage 14, above) having a diameter d (in centimeters) and a length L (in centimeters) such that, for any value of chamber A gas flow rate Q (in cubic centimeters per second), diameter d and length L are defined by the area substantially bounded by the following equations:

$$L \leq (0.127 \cdot t_R \cdot Q) d^2 \qquad (Eq.\ 1)$$

where $T_R$ = gas clearing response time in the second chamber B (in seconds);

$$L \geq (7.85 \cdot D_{AB} \cdot d^2)/Q \qquad (Eq.\ 2)$$

where $D_{AB}$ = mass diffusivity (in square centimeters per second); and $$L \leq (16d - D/2) \qquad (Eq.\ 3)$$

where D is the diameter of second chamber B (cavity 13, above) (in centimeters)

Figure 5:
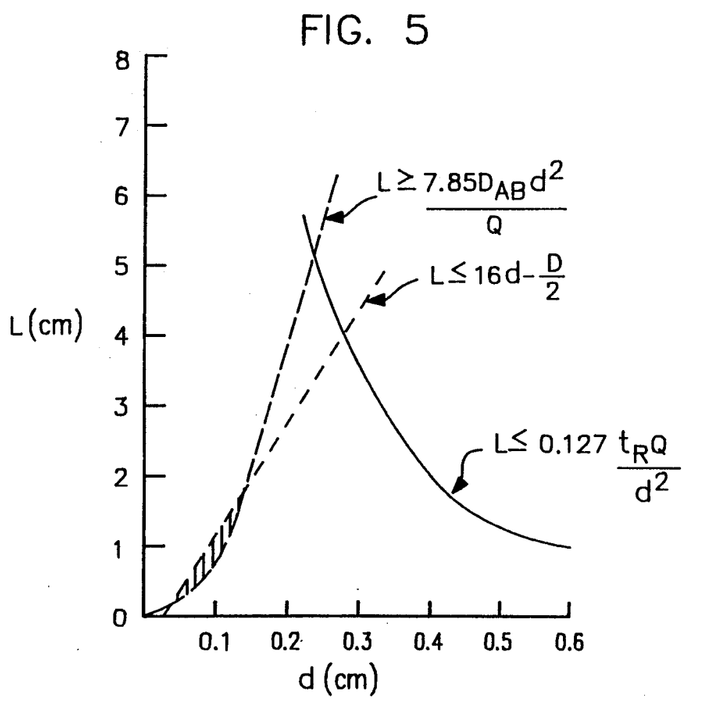
FIG. 5 is a graphical representation of the operation parameters of the present invention for a first exemplary gas flow rate.
Figure 6:
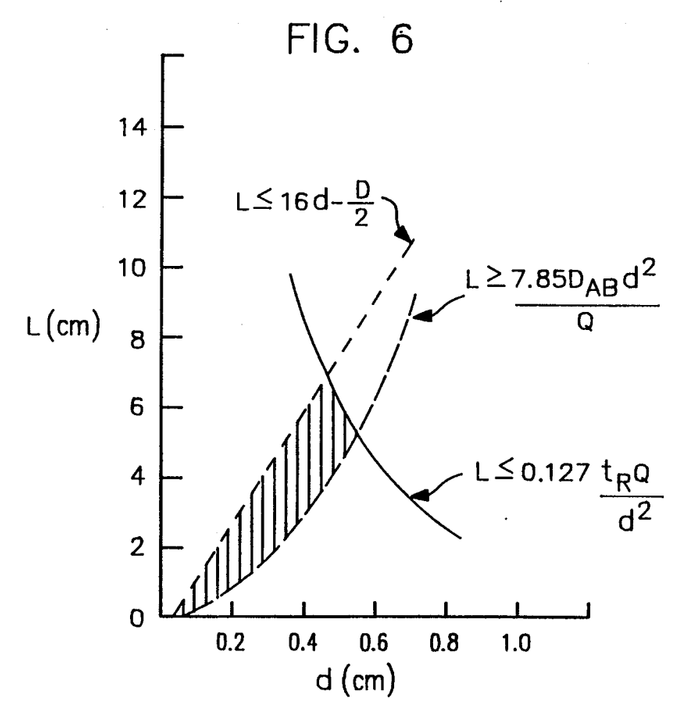
FIG. 6 is a graphical representation of the operation parameters of the present invention for a second exemplary gas flow rate.

Thus, glow discharge chamber 1 can be configured for any chamber A gas flow rate Q as long as first chamber A has a length L and a diameter d satisfying the area substantially bounded by the above three equations. Referring specifically to FIGS. 5-6, two such bounded areas are shown. FIG. 5 shows diameter d and length L values for a chamber A of glow discharge chamber 1 for use with a chamber A gas flow rate Q of 25 cubic centimeters per second. FIG. 6 shows diameter d and length L values for a chamber A of glow discharge chamber 1 for use with a chamber A gas flow rate Q of 125 cubic centimeters per second. It is to be understood, however, that FIGS. 5-6 only disclose diameter d and length L values for exemplary chamber A flow rates Q, and that the subject invention encompasses all diameter d and length L dimensions for all chamber A gas flow rates Q that are attainable with equations 1-3, as derived below.

Specifically, Eq. 1 is derived based on glow discharge stability and the response time of the glow discharge chamber 1. To insure adequate discharge stability:

$$D \geq 0.6 \qquad (Eq.\ 4)$$

where D = the diameter of second chamber B (in centimeters).

Regarding response time, for a spectrometer to measure gas concentration with a response time $t_R$ of 10% to 90% or less, the total flow $Q_T$ through second chamber B (from one or more chambers A) must be sufficiently high to clear second chamber B about 10 times within the time period $t_R$, or:

$$Q_T \geq \frac{10}{t_R} \cdot \frac{\pi D^2}{4} \cdot S \quad \text{(Eq. 5)}$$

where $Q_T$ = total gas flow through second chamber B (in cubic centimeters per second);

$t_R$ = response time (in seconds);

D = the diameter of second chamber B (in centimeters); and

S = the distance separating cathode 15 and anode 19 (in centimeters).

For minimum gas flow $Q_{Tmin}$ where Eq. 1 above is satisfied (i.e., D = 0.6 centimeters), and where $S_{min}$ = 0.6 centimeters and $T_R$ = 0.1 seconds, $Q_{Tmin}$ = 17.0 cubic centimeters per second. For typical gas flow $Q_{Typ}$ where D = 1.0 centimeters, S = 1.0 centimeters, and $t_R$ = 0.1 seconds, $Q_{Typ} \geq 78.5$ cubic centimeters per second.

Applying the same response time considerations to first chamber A that were employed to derive Eq. 5 for second chamber B, above, results in Eq. 1:

$$Q \geq \frac{10}{t_R} \cdot \frac{\pi d^2}{4} \cdot L \quad \text{(Eq. 6)}$$

where

Q = gas flow rate in chamber A (in cubic centimeters per second);

$t_R$ = response time (in seconds);

d = diameter of first chamber A (in centimeters); and

L = length of first chamber A (in centimeters).

Solving Eq. 6 for L provides Eq. 1, where:

$$L \leq (0.127 \cdot t_R Q)/d^2 \quad \text{(Eq. 1)}$$

Eq. 2, above, is derived based on mass diffusivity considerations. Chamber A gas flow rate Q must be high enough to prevent diffusion of the sputtered particles from cathode 15 onto window 5. This is achieved by insuring that the Peclet number, which is the ratio of directed flow to diffusive flow, satisfies the following equation:

$$P_e = U \cdot L/D_{AB} \geq 10 \quad \text{(Eq. 7)}$$

where $P_e$ = Peclet number;

U = directed velocity in first chamber A
 = $4Q/\pi d^2$; and $$D_{AB} = 0.00186 \frac{\sqrt{T^3 \left(\frac{1}{M_A} + \frac{1}{M_B}\right)}}{P \cdot \rho_{AB}^2 \cdot \Omega_{D,AB}}$$

where

T = temperature (in °K);

P = pressure (in atmospheres);

M = molecular weight;

$\rho_{AB}$ = interaction distance between molecules (in Angstroms); and $\Omega_{D,AB}$ = a dimensionless relationship between temperature and intermolecular field.

Solving Eq. 7 for L, where $U = 4Q/\pi d^2$, and $P_e \geq 10$ provides Eq. 2:

$$L \geq (7.85 D_{AB} d^2)/Q \quad \text{(Eq. 2)}$$

Using empirical data known in the art provides $\rho_{AB}$ and $\Omega_{D,AB}$ of $D_{AB}$ for oxygen and nitrogen. If T = 298° K and P = 0.6/760 atmospheres, the $D_{AB}$ = 275 square centimeters per second, and Eq. 2 is:

$$L \geq 2160 \, d^2/Q \quad \text{(Eq. 8)}$$

Eq. 3 above is derived based on light collection considerations. The light collection angle α from negative glow radiation 17 through window 5 must be large enough to provide an adequate signal to noise ratio. Specifically, α must satisfy the following equation:

$$\tan \alpha = \frac{d}{\left(\frac{D}{2} + L\right)} \geq \frac{1}{16} \quad \text{(Eq. 9)}$$

where

α = the light collection angle;

d = diameter of first chamber A (in centimeters);

D = diameter of second chamber B (in centimeters); and

L = length of first chamber A (in centimeters)

Eq. 9 is derived based on photodetectors with a maximum quantum efficiency of about 25% at the ultraviolet end of the spectrum to 100% at the near infrared end. Additionally, Eq. 9 assumes that a signal to noise ratio of about 100 is required to obtain 1% resolution for gas analysis. Solving Eq. 9 for L results in Eq. 3:

$$L \leq (16d - D/2) \quad \text{(Eq. 3)}$$

Referring again to FIGS. 5–6, in addition to the respective chamber A gas flow rate Q values of 25 cubic centimeters per second and 125 cubic centimeters per second, FIGS. 5–6 also are based on the following exemplary parameters: $D_{AB}$ = 275 square centimeters per second, D = 1 centimeter, $t_R$ = 0.1 second, and P = 0.6 torr.

It is understood that the above parameters are only exemplary and that the present invention encompasses additional diameter d and length L values for first chamber A for the above exemplary chamber A flow rate Q values (as well as other chamber A flow rate Q values) regardless of the $D_{AB}$, D, $t_R$, and P values employed as long as Eqs. 1–3 are satisfied.

While the above derivation pertains to only one chamber A (passage 14), it is also apparent that if more than one first chambers A (passages 14) are employed (for example, four as shown in FIGS. 1–6), the above chamber A flow rate Q is merely multiplied by the number of chambers A actually employed to obtain total flow rate $Q_T$. For example, if four chambers A (passages 14) are employed, the chamber A flow rate Q value is multiplied by four to derive total flow rate $Q_T$. However, since the above derivations of Eqs. 1–3 are based on chamber A flow rate Q, not total flow rate $Q_T$, Eqs. 1–3 are valid for a glow discharge chamber 1 having any number of chambers A.

Referring to FIGS. 1–4, the glow discharge chamber of the present invention, allows calibration of a glow discharge emission spectrometer employing the present invention in a two step process employing only two gasses.

First, the sample gas inlet flow is shut-off and a flow background gas consisting of about 20 percent oxygen and 80 percent nitrogen is passed through glow discharge chamber 1 in the manner described above such that spectral analysis is performed on the background gas by the glow discharge emission spectrometer.

Next a flow of span gas consisting of about 95 percent oxygen and 5 percent carbon dioxide is passed through glow discharge chamber 1 in the manner described above such that spectral analysis is performed on the span gas by the glow discharge emission spectrometer.

While particular embodiments of the present invention have been described in some detail herein above, changes and modifications may be made in the illustrated embodiments without departing from the spirit of the invention.

I claim:

1. A glow discharge chamber for a glow discharge emission spectrometer comprising:
   a housing having a cavity;
   a gas inlet to said cavity;
   a gas outlet adapted to be connected to means for providing relatively low pressure to produce flow of gas through said cavity;
   an anode in said cavity and adjacent to said gas outlet;
   a cathode in said cavity such that a voltage differential between said cathode and said anode causes gas in said cavity to emit negative glow radiation adjacent to said cathode, said cathode is a conductor selected from the group consisting of titanium, and its carbide;
   a radiation transmissive gas retaining window in said housing adjacent said gas inlet through which negative glow radiation is passed for spectral analysis; and
   said cathode and anode arranged in said cavity so that sputtered oxides of said cathode are channeled away by said flow of gas from said window.

2. The glow discharge chamber of claim 1 further comprising:
   a plurality of said windows; and
   a plurality of said gas inlets to said cavity, each of said gas inlets being adjacent to one of said windows, so that sputtered oxides of said cathode are channeled away from said windows by non-axial flow of gas from said gas inlets to said gas outlet.

3. A glow discharge chamber for a glow discharge emission spectrometer comprising:
   a housing having a first substantially elongate chamber and a second substantially elongate chamber connected to said first chamber;
   a gas inlet to said first chamber;
   a gas outlet in said second chamber, said gas outlet adapted to be connected to means for providing relatively low pressure to produce gas flow Q in cubic centimeters per second through said first chamber;
   an anode in said second chamber and adjacent to said gas outlet;
   a cathode in said second chamber such that a voltage differential between said cathode and said anode causes gas in said first chamber to emit negative glow radiation adjacent to said cathode;
   a radiation transmissive gas retaining window in said housing and adjacent said first chamber through which negative glow radiation adjacent said cathode is passed for spectral analysis, said cathode and anode arranged in said second chamber so that sputtered oxides of said cathode are channeled away by said gas flow Q from said window, said first chamber having a cross-section d in centimeters and a length L in centimeters for a given gas flow Q where cross-section d and length L are defined by the area substantially bounded by the equations:

$$L \leq (0.127 \cdot t_R \cdot Q)/d^2$$

wherein $t_R$ = gas clearing response time (in seconds);

$$L \geq (7.85 \cdot D_{AB} \cdot d^2)/Q$$

wherein $D_{AB}$ = mass diffusivity (in cm² per second); and $$L \leq (16d - D/2)$$

wherein D = cross-section of said second chamber.

4. The glow discharge chamber of claim 3 wherein gas flow Q is about 25 cubic centimeters per second.

5. The glow discharge chamber of claim 4 wherein the gas clearing response time tR of said glow discharge chamber is about 0.1 seconds.

6. The glow discharge chamber of claim 4 wherein the mass diffusivity $D_{AB}$ is about 275 square centimeters per second.

7. The glow discharge chamber of claim 4 wherein the cross-section D of said second chamber is about 1.0 centimeters.

8. The glow discharge chamber of claim 4 wherein the pressure P in said glow discharge chamber is about 0.6 torr.

9. The glow discharge chamber of claim 4 wherein the temperature T in said glow discharge chamber is about 298° K.

10. The glow discharge chamber of claim 3 wherein gas flow Q is about 125 cubic centimeters per second.

11. The glow discharge chamber of claim 10 wherein the gas clearing response time tR of said glow discharge chamber is about 0.1 seconds.

12. The glow discharge chamber of claim 10 wherein the mass diffusivity $D_{AB}$ is about 275 square centimeters per second.

13. The glow discharge chamber of claim 10 wherein the cross-section D of said second chamber is about 1.0 centimeters.

14. The glow discharge chamber of claim 10 wherein the pressure P in said glow discharge chamber is about 0.6 torr.

15. The glow discharge chamber of claim 10 wherein the temperature T in said glow discharge chamber is about 298° K.

16. The glow discharge chamber of claim 3 further comprising:
   a plurality of said windows; and
   a plurality of said gas inlets to said first chamber, each of said gas inlets being adjacent to one of said windows, so that sputtered oxides of said cathode are channeled away from said windows by non-axial flow of gas from said gas inlets to said gas outlet.

17. The glow discharge chamber of claim 3 wherein said cathode is a conductor selected from the group consisting of titanium, and its carbide.

18. A system for providing relatively low pressure to a glow discharge chamber for a glow discharge emission spectrometer, said system including an atmospheric inlet, said system comprising:

pump means for providing relatively low pressure;

a gas line connecting said pump means to a gas outlet of a glow discharge chamber; and a control valve in said gas line for adjustment of glow discharge chamber pressure from about 0.4 torr to about 0.7 torr with a gas flow rate at the atmospheric inlet of about 6 milliliters per minute at about 760 torr pressure and at about 298° K, and for adjustment of gas flow rate at the atmospheric inlet from about 3 milliliters per minute to about 7 milliliters per minute at about 760 torr pressure and 298° K with a glow discharge chamber pressure of about 0.6 torr.

19. A method of forming a glow discharge region in a gas spectrometer, the improvement comprising:

applying a voltage differential between an anode and cathode in a cavity through which gas to be analyzed for spectral content is passed under a flow inducing pressure difference to cause gas in said cavity to emit negative glow radiation adjacent to said cathode; and channeling said flow away from a radiation transmissive gas retaining spectral viewing window in said cavity so as to divert sputtered cathodic oxides from depositing on and occluding said window, wherein said gas to be analyzed includes a background gas of about 20 percent oxygen and about 80 percent nitrogen, and a span gas of about 95 percent oxygen and about 5 percent carbon dioxide, said background gas being passed through said cavity prior to said span gas so that said gas spectrometer is calibrated based on negative glow radiation readings of said background gas and said spun gas.

* * * * *